United States Patent [19]

Haberkorn et al.

[11] Patent Number: 4,568,674
[45] Date of Patent: Feb. 4, 1986

[54] ANTI-COCCIDAL AGENTS 1-[4-(BENZOTHIA- OR -OXAZOL-2-YLTHIO- OR -2-YLOXY)PHENYL]-1,3,5-TRIAZINE-2,4,6-(1H,3H,5H)-TRIONE DERIVATIVES, COMPOSITIONS, AND METHOD OF USE THEREOF

[75] Inventors: Axel Haberkorn, Wuppertal; Heinrich Kölling, Haan, both of Fed. Rep. of Germany; Toyohiko Kume; Shinpei Kuyama, both of Tokyo, Japan

[73] Assignee: Bayer Aktiengesellschaft, Leverkusen, Fed. Rep. of Germany

[21] Appl. No.: 700,366

[22] Filed: Feb. 11, 1985

[30] Foreign Application Priority Data

Feb. 15, 1984 [DE] Fed. Rep. of Germany ....... 3405241

[51] Int. Cl.$^4$ .................. C07D 251/30; A01N 43/66; A61K 31/53
[52] U.S. Cl. .................................... 514/241; 544/221; 544/222; 426/532
[58] Field of Search ............... 544/221, 222; 426/532; 514/241

[56] References Cited

U.S. PATENT DOCUMENTS 2,733,243 1/1956 D'Amico ........................... 544/219
3,933,814 1/1976 Haberkorn et al. ............... 544/221

FOREIGN PATENT DOCUMENTS 0043573 4/1981 European Pat. Off. ........... 548/165
2225071 12/1972 Fed. Rep. of Germany ...... 548/165
998368 7/1965 United Kingdom ............... 544/219

OTHER PUBLICATIONS

Chemical Abstracts, vol. 86, No. 15, Apr. 1977, "Mixed N-phenyl and N-dialkyl Isocyanurates", p. 507, Summary 106534T.

Primary Examiner—Henry R. Jiles
Assistant Examiner—J. G. Mullins
Attorney, Agent, or Firm—Sprung Horn Kramer & Woods

[57] ABSTRACT

1-[4-(Benzothia- or -oxazol-2-ylthio- or -2-yloxy)-phenyl]-1,3,5-triazine-2,4,6(1H,3H,5H)-triones of the formula

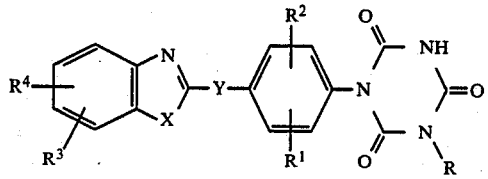

in which
R is lower alkyl,
$R^1$ and $R^2$ each independently is hydrogen, halogen, alkyl or alkoxy,
$R^3$ and $R^4$ each independently is hydrogen, halogen, alkyl, alkoxy, alkylthio, fluoroalkyl, fluoroalkoxy or fluoroalkylthio, and
X and Y each independently is sulphur or oxygen,
or salts thereof, combat coccidioses, especially in poultry.

6 Claims, No Drawings

ANTI-COCCIDAL AGENTS 1-[4-(BENZOTHIA- OR -OXAZOL-2-YLTHIO- OR -2-YLOXY)PHENYL]-1,3,5-TRIAZINE-2,4,6-(1H,3H,5H)-TRIONE DERIVATIVES, COMPOSITIONS, AND METHOD OF USE THEREOF

The present invention relates to 1-[4-(benzothia- or -oxazol-2-ylthio- or -2-yloxy)phenyl]-1,3,5-triazine-2,4,6-(1H,3H,5H)-triones, a process for their preparation and their use as medicaments, in particular as anticoccidial agents for humans and for various species of animals.

It has already been disclosed that α-(4-phenylthio-phenyl)-1,2,4-triazine-3,5-diones have an action for combating coccidiosis. However, the action is not satisfactory in all cases, especially when low concentrations are used.

The new 1-[4-(benzothia- or -oxazol-2-ylthio- or -2-yloxy)phenyl]-1,3,5-triazine-2,4,6(1H,3H,5H)-triones of the formula (I)

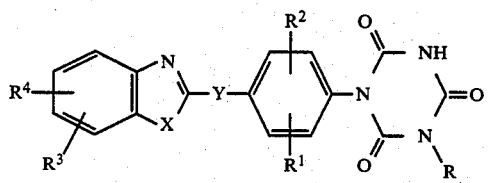

in, which
R represents lower alkyl,
$R^1$ and $R^2$ are identical or different and represent hydrogen, halogen, alkyl or alkoxy,
$R^3$ and $R^4$ are identical or different and represent hydrogen, halogen, alkyl, alkoxy, alkylthio, fluoroalkyl, fluoroalkoxy or fluoroalkylthio and
X and Y are identical or different and represent sulphur or oxygen,
and their salts, have been found.

The compounds of the formula I and their salts can be prepared by a process in which a substituted urea of the formula

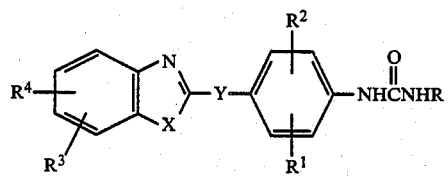

in which R, $R^1$, $R^2$, $R^3$, $R^4$, X and Y have the abovementioned meaning,
is reacted with a carbonyl isocyanate of the formula

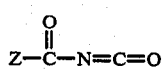

in which Z represents halogen, alkoxy or aryloxy,
and, in the case of the salts, a compound of the formula I is reacted with a base.

The substituted ureas of the formula II are new. They can be prepared by a process in which
(a) a lower alkyl isocyanate is reacted with an amine of the formula IV

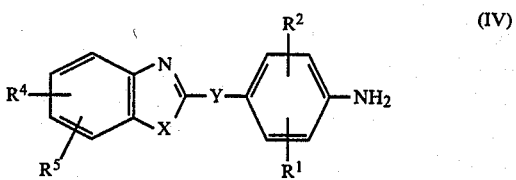

in which $R^1$, $R^2$, $R^3$, $R^4$, X and Y have the abovementioned meanings,
or
(b) a lower alkylamine is reacted with an isocyanate of the formula V

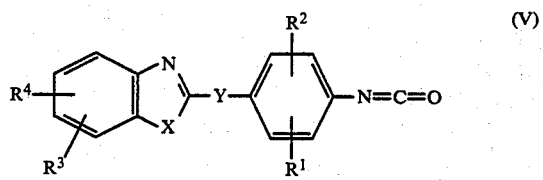

in which $R^1$, $R^2$, $R^3$, $R^4$, X and Y have the abovementioned meanings,
or
(c) a urea of the formula VI

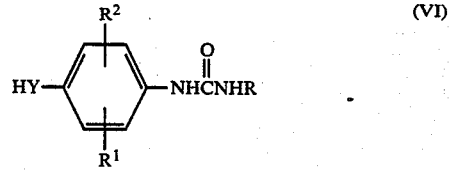

in which R, $R^1$, $R^2$ and Y have the abovementioned meanings,
is reacted with a compound of the formula VII

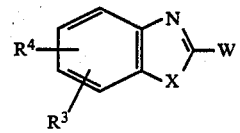

in which
$R^3$, $R^4$ and X have the abovementioned meanings and
W designates chlorine or bromine,
in the presence of a suitable base.

Some of the compounds of the formula IV are known (*Chemical Abstracts* CA 93-71689; 72-134130; 78-58423). New compounds of the formula IV can be prepared by methods which are known per se (DE-OS (German Published Specification) 2,225,071).

The compounds of the formula V are new. They are prepared, for example, by reacting compounds of the formula IV with phosgene or trichloromethoxycarbonyl chloride in a manner which is known per se.

The compounds of the formula VI are known, or they can be prepared by methods which are known per se (*J. Med. Chem.* 1977, 20(5), pages 705–708, and Chemical Abstracts CA 96-6442; 91-193023; 87-78230).

The compounds of the formula VII are known, or they can be prepared by methods which are known per se (J.O.C. 19, 758; and EP-OS (European Published Specification) 43,573).

Preferred compounds of the formula I are those in which
R represents $C_{1-4}$-alkyl,
$R^1$ and $R^2$ represent hydrogen, chlorine or $C_{1-4}$-alkyl, in particular in the 3'- and 5'-position,
$R^3$ represents halogen, $C_{1-4}$-alkyl, $C_{1-4}$-alkoxy, $C_{1-4}$-halogenoalkoxy, $C_{1-4}$-halogenoalkyl, $C_{1-4}$-alkylthio or $C_{1-4}$-halogenoalkylthio,
$R^4$ represents hydrogen or halogen, in particular chlorine,
X represents O or S and
Y represents O or S.

Compounds of the formula I which may be mentioned in particular are those
in which
R represents methyl, ethyl or propyl,
$R^1$ and $R^2$ represent hydrogen, chlorine or methyl, in particular in the 3'- or 5'-position,
$R^3$ represents fluorine, chlorine, bromine, iodine, methyl, ethyl, methoxy, ethoxy, methylthio, trifluoromethyl, trifluoromethoxy or trifluoromethylmercapto,
$R^4$ represents hydrogen or chlorine and
X and Y represent O or S.

The compounds of the formula I and their salts can advantageously be used for combating coccidioses in humans and animals, especially in poultry and domestic animals. In addition to their excellent action, their rapid degradation in the organism should be mentioned.

The reaction of the compounds of the formula II with a carbonyl isocyanate of the formula III can be represented by the following equation:

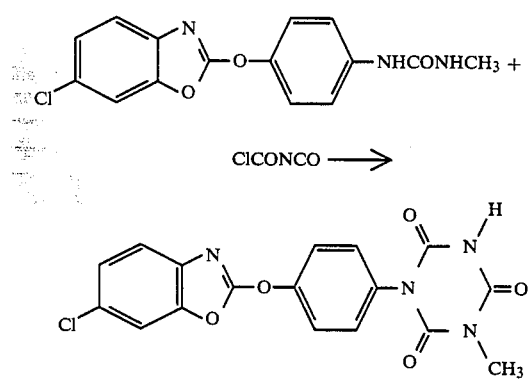

Preferred compounds of the formula II which may be mentioned are those
in which
R represents $C_{1-4}$-alkyl, in particular methyl, ethyl or propyl,
$R^1$ and $R^2$ represent hydrogen, chlorine or methyl, the substituents being, in particular, in the 5'- and 3'-position,
$R^3$ represents fluorine, chlorine, bromine, iodine, $C_{1-4}$-alkyl, in particular methyl, $C_{1-4}$-alkoxy, in particular methoxy or ethoxy, $C_{1-4}$-halogenoalkoxy, in particular trifluoromethoxy, $C_{1-4}$-halogenoalkyl, in particular trifluoromethyl, $C_{1-4}$-alkylmercapto, in particular methylmercapto, or $C_{1-4}$-halogenoalkylmercapto, in particular trifluoromethylmercapto,
$R^4$ represents hydrogen or halogen, in particular chlorine,
X represents oxygen or sulphur and
Y represents oxygen or sulphur.

The preferred carbonyl isocyanate which may be mentioned is chlorocarbonyl isocyanate.

The reaction is carried out in inert organic solvents. These include hydrocarbons, such as, in particular, benzene, toluene and xylene, halogenated hydrocarbons, such as chlorobenzene, dichlorobenzene, methylene chloride and chloroform, and ethers, such as tetrahydrofuran and dioxane.

The reaction is usually carried out under normal pressure and at a temperature between 0° and 150° C., in particular at 80°-120° C.

The compounds are used in approximately equimolar amounts. It may be advantageous to use the carbonyl isocyanate in excess.

Salt formation is effected by reacting the compounds of the formula I with an inorganic or organic base. For this, bases are used which lead to salts which do not harm the warm-blooded organism in the concentration customary for coccidiosis agents.

Examples of bases which may be mentioned are: potassium hydroxide, sodium hydroxide, ammonia and methylamine.

The compounds of the formula II are new.

Their preparation from compounds of the formula IV and alkyl isocyanates can be represented by the following equation:

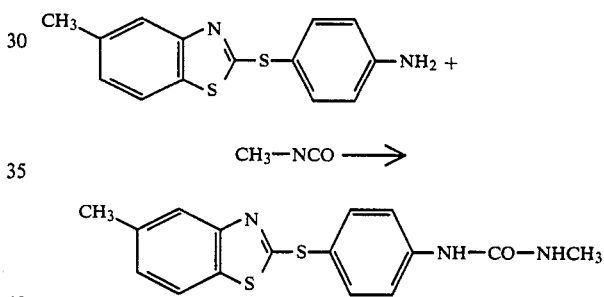

Compounds of the formula IV in which $R^1$, $R^2$, $R^3$ and $R^4$ have the abovementioned preferred meaning are preferably used.

Preferred alkyl isocyanates which may be mentioned are: methyl, ethyl and propyl isocyanate.

The reaction is in general carried out in the presence of an inert diluent. Preferred diluents which may be mentioned are those mentioned for the process for the preparation of the compounds of the formula I.

The reaction is carried out at temperatures of 0°-150° C., in particular at 20°-80° C.

The reaction is preferably carried out under normal pressure.

The compounds are employed in approximately equimolar amounts. An excess of the isocyanate may be advantageous.

The compounds of the formula II are also obtained by reacting compounds of the formula V with alkylamines. The reaction can be represented by the following equation:

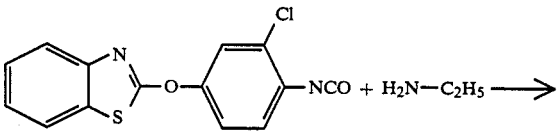

-continued

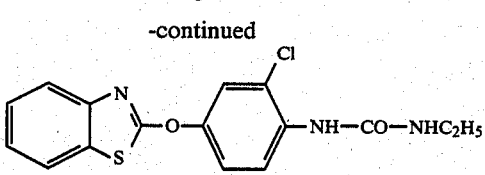

Preferred compounds of the formula V are those in which $R^1$, $R^2$, $R^3$ and $R^4$ have the meanings mentioned above as preferred.

The reaction is carried out in a manner which is known per se, for example in the abovementioned diluents. The reaction conditions can also be chosen as mentioned above.

Compounds of the formula II are also obtained by reacting compounds of the formula VI with compounds of the formula VII. The reaction can be represented by the following equation:

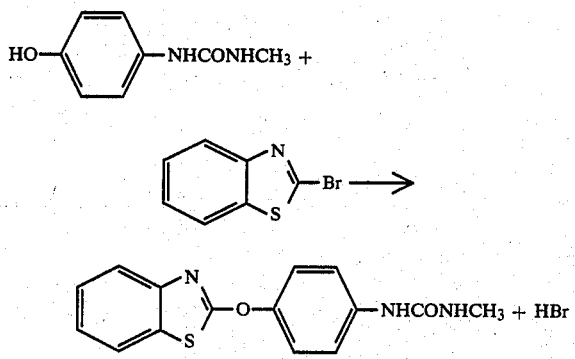

Preferred compounds of the formula VI are those in which R, $R^1$, $R^2$ and Y have the meanings mentioned above as preferred.

Preferred compounds of the formula VII are those in which $R^3$ and $R^4$ have the meanings mentioned above as preferred.

The reaction is carried out, for example, in one of the abovementioned diluents. The reaction is carried out in the presence of a base. Bases which may be mentioned are inorganic and organic bases, such as, for example, KOH, NaOH, Ca(OH)$_2$, pyridine and triethylamine.

The compounds of the formulae VI and VII and the base are brought together in approximately equimolar amounts. A slight excess of one or the other of the components has no significance on the yield.

The compounds according to the invention and their salts have a good activity against Coccidia in poultry, for example *Eimeria tenella* (caecal coccidiosis in poultry), *E. acervulina, E. brunetti, E. maxima, E. mitis, E. mivati, E. necatrix* and *E. praecox* (coccidiosis of the small intestine in poultry).

The formulations can also be used for the prophylaxis and treatment of other types of coccidiosis infections in domestic poultry. The compounds according to the invention moreover exhibit a powerful activity against Coccidia infections in mammals. The compounds can furthermore be used in the treatment or prophylaxis of toxoplasmosis, both in the treatment of cats, which are responsible for excretion of the infectious stages (oocysts), and for the treatment of infected humans. The new compounds can also be used for the treatment and prophylaxis of Sarcocystis infections, both in the obligate intermediate host (for example pigs, cattle, sheep) and in the definitive host (for example humans, cats, dogs).

Coccidia infections can lead to severe losses in domestic animals and are a real problem in the rearing of poultry and mammals such as cattle, sheep, rabbits and dogs. The action of the known agents against coccidiosis is in most cases limited to a few species of poultry. The treatment and prophylaxis of coccidiosis in mammals has hitherto been a major unsolved problem.

The medicament formulations according to the invention contain a larger or smaller amount, for example 0.1% to 99.5%, preferably 0.5% to 90%, of at least one compound of the formula I according to the invention or their salts, in combination with a pharmaceutically acceptable, non-toxic inert extender or excipient, the excipient containing one or more solid, semi-solid or liquid diluents, extenders, fillers and formulation adjuvants which are non-toxic, inert and pharmaceutically acceptable. These medicament formulations are preferably in the form of dosage units, that is to say physically discrete units which contain a predetermined amount of the medicament corresponding to a fraction or a multiple of the dose which, according to calculation, produces the desired therapeutic action. The dosage units can contain one, two, three, four or more individual doses or, alternatively, one half, one third or one quarter of an individual dose. An individual dose preferably contains an amount which is sufficient to cause the desired therapeutic action, when used once, after administration of one or more dosage units according to a predetermined dosage treatment prescription, usually a whole, one half, one third or one quarter of the daily dose, administered once, twice, three times or four times daily. Other therapeutic agents can also be present.

Oral administration can be effected using solid or liquid dosage unit forms, for example powders, tablets, dragees, capsules, granules, suspensions, solutions and the like.

Powders are prepared by grinding the compounds to a suitable fine size and mixing the ground material with a pharmaceutical excipient ground in a similar manner, such as an edible carbohydrate, for example starch, lactose, sucrose, glucose or mannitol. Sweeteners, aromatizing agents, preservatives, dispersing agents and colorants can also be present.

Capsules are prepared by formulating a powder mixture, as has been described above, and filling shaped gelatine shells with the mixture. Lubricants and smoothing agents, for example colloidal silicon dioxide, talc, magnesium stearate, calcium stearate or solid polyethylene glycol, can be added to the powder mixture before the filling operation. A disintegrating agent or solubilizing agent, for example agar-agar, calcium carbonate or sodium carbonate, can also be added in order to improve the availability of the medicament when the capsule is taken.

Tablets are formulated, for example, by preparation of a powder mixture, granulation or bead formation, addition of a lubricant and disintegrating agent and pressing to tablets. A powder mixture is prepared by mixing the compound, which has been comminuted in a suitable manner, with a diluent or extender or a base in the manner described above and, if desired, with a binder, such as carboxymethylcellulose, an alginate, gelatine or polyvinylpyrrolidone, a solution retarder, for example paraffin, an absorption accelerator, for example a quaternary salt, and/or an absorbent, such as bentonite, kaolin or dicalcium phosphate. The powder mixture can be granulated by wetting with a binder, such as syrup, starch paste, mucus of gum arabic or solutions of cellulose materials or polymeric materials, and pressing the mixture through a sieve. As an alternative to granulation, the powder mixture can be passed through the tablet-making machine and the incompletely shaped beads thereby obtained can be broken into granules. The granules can be lubricated by addition of stearic acid, a stearic salt, talc or mineral oil to prevent them from sticking to the tablet-forming nozzles. The lubricated mixture is then pressed to tablets. The medicaments can also be combined with free-flowing inert excipients and pressed directly to tablets, without passing through granulation or beading stages. A clear or opaque protective coating consisting of a sealing coating of shellac, a coating of sugar or polymeric material and a polishing wax coating can be provided. Colorants can be added to these dosages to differentiate between different dosage units.

Oral liquids, for example solutions, syrups and elixirs, can be prepared in dosage unit form such that a given amount contains a predetermined amount of the compound. Syrups can be prepared by dissolving the compound in an aqueous sucrose solution which has been rendered palatable in a suitable manner, while elixirs can be prepared by using a non-toxic alcoholic excipient. Suspensions can be prepared by dispersing the compound in a non-toxic excipient. Solubilizing agents and emulsifiers, for example ethoxylated isostearyl alcohols and polyoxyethylene sorbitol esters, preservatives, additives which impart flavor, for example peppermint oil or saccharin, and the like can also be added.

If appropriate, dosage unit formulations for oral administration can be prepared in the form of microcapsules. The formulation can also be prepared such that the release is delayed or sustained, for example by encasing or embedding the fine-particled material in polymers, wax or the like.

Parenteral administration can be effected using liquid dosage unit forms, for example sterile solutions and suspensions, which are envisaged for subcutaneous, intramuscular or intravenous injection. These formulations are prepared by suspending or dissolving a measured amount of the compound in a non-toxic liquid excipient suitable for the injection, for example an aqueous or oily medium, and sterilizing the suspension or solution. Alternatively, a measured amount of the compound is introduced into an ampule and the ampule and its contents are sterilized and closed by fusion. An associated ampule or an associated excipient can be provided for mixing before administration. Non-toxic salts and salt solutions can be added in order to render the injection solution isotonic. Stabilizers, preservatives and emulsifiers can also be added.

Rectal administration can be effective using suppositories in which the compound is mixed with low-melting, water-soluble or insoluble solids, for example polyethylene glycol, cacao butter, higher esters, for example myristyl palmitate, or mixtures thereof.

Topical application can be effected using solid dosage unit forms, for example powders, or liquid or semi-liquid dosage unit forms, for example solutions, suspensions, ointments, pastes, creams and gels. The powders are formulated using excipients, such as talc, bentonite, silicic acid, polyamide powder and the like. Excipients in addition to those described above, for example polyethylene glycol, vegetable and mineral oils and alcohols, for example isopropanol, can be added to the liquid and semi-liquid formulations. Other auxiliaries, for example emulsifiers, prservatives, coloring agents, fragrances and the like, can also be present. The formulations can also be applied as aerosols, in which case the customary propellants, for example the chlorofluorohydrocarbons, are used.

The preferred daily dose is 25 mg to 25 g of the active content.

While oral, parenteral (that is to say intramuscular, intraperitoneal and intravenous) and rectal administration and topical application belong to the administration routes, oral administration is particularly preferred.

The invention furthermore relates to feedstuffs and foodstuffs containing 5 to 5,000 ppm, preferably 50 to 250 ppm, of a compound according to the invention in combination with a suitable edible material, for example with the feedstuff for hens described by the following formulation:

| | |
|---|---|
| 52.000% | of shredded fodder grain |
| 17.995% | of shredded soy bean |
| 5.000% | of corn gluten feedstuff |
| 5.000% | of whole wheat flour |
| 3.000% | of fish meal |
| 3.000% | of tapioca meal |
| 3.000% | of green lucerne meal |
| 2.000% | of ground wheatgerm |
| 2.000% | of soy oil |
| 1.600% | of fishbone meal |
| 1.500% | of whey powder |
| 1.400% | of calcium carbonate for feedstuffs and foodstuffs |
| 1.000% | of calcium phosphate for feedstuffs and foodstuffs |
| 1.000% | of molasses |
| 0.500% | of brewers' yeast |
| 0.005% | of 1-[4-(6-chlorobenzothiazol-2-ylthio)-phenyl]-1,3,5-triazine-2,4,6(1H,3H,5H)—trione |
| 100.000% | |

Such a feedstuff and foodstuff can be used either for curing purposes or for prophylactic purposes.

The present invention furthermore relates to a concentrate or a premix containing 1 to 30% by weight, preferably 10 to 20% by weight, of a compound according to the invention mixed with an edible organic or inorganic carrier, for example corn flour or corn and soy bean flour, or mineral salts, which preferably contain a small amount of an edible dust-prevention oil, for example corn oil or soy bean oil. The premix thereby obtained can then be added to the complete poultry feedstuff before this is fed to the animals.

The compounds according to the invention can also be mixed with the drinking water for the animals for mass treatment or prophylaxis of coccidiosis.

The feedstuff can be used either for curing purposes or for prophylactic purposes. For curing treatment and prophylaxis of coccidiosis in poultry, in particular in hens, ducks, geese and turkeys, 25 to 100 ppm, preferably 50 to 100 ppm, of a compound according to the invention is mixed with a suitable edible material, for example a nutritive feedstuff. If desired, these amounts can be increased, especially if the compound is tolerated well by the recipient.

For the treatment of individual animals, for example in the case of the treatment of coccidiosis in mammals or of toxoplasmosis, amounts of 5 to 250 mg/kg of body weight are preferably administered daily, in order to achieve the desired effective results. Nevertheless, it may at times be necessary to deviate from the amounts mentioned, in particular as a function of the body weight of the test animal or the nature of the method of administration, but also because of the animal species and its individual reaction to the medicament or the nature of the formulation and the time or interval over which it is administered. Thus, in certain cases it may be sufficient to manage with less than the abovementioned minimum amount, while in other cases the upper limit mentioned must be exceeded. Where relatively large amounts are administered, it may be appropriate to divide these into several individual administrations over the course of the day.

The coccidiostatic activity of compounds which are representative of the compounds according to the invention is illustrated in Table 1, where an *Eimeria tenella* (caecococcidiosis/hens), *Eimeria acervulina* and *Eimeria maxima* (coccidiosis of the small intestine in hens) are mentioned as examples of the activity in the case of coccidiosis in poultry, while *Eimeria falciformis* (coccidiosis/mice) is given as a Coccidium in mammals.

For example, if chicks 9 to 11 days old are infected with 4,000 sporulated oocysts of highly virulent strains of *E. acervulina, E. maxima* and *E. tenella*, the pathogens of intestinal coccidiosis, the untreated comparison animals excrete 300,000 to 500,000 oocysts/g of droppings daily from the fifth to the ninth day after the infection. The weight increase is considerably reduced during the course of the disease, and serious, macroscopically detectable pathological changes occur, chiefly in the intestines, which can lead to serious haemorrhagic diarrhoea, and the chicks may die. On investigating the effectiveness against *E. acervulina, E. maxima* and *E. tenella*, the compounds according to the invention were administered 3 days before the infection up to 8 days after the infection (end of the experiment).

The number of oocysts was determined with the aid of a McMaster chamber (see Engelbrecht et al. "Parasitologische Arbeitsmethoden in Medizin und Vererinärmedizin" ("Parasitological methods in medicine and veterinary medicine"), page 172, Akademie-Verlag Berlin (1965)).

Treatment of infection by *Eimeria falciformis* in mice, which is mentioned as an example of coccidiosis in mammals, took place on the first, second, third, sixth, seventh and eighth day after the infection. Infection was effected with 10,000 sporulated oocysts per mouse (weight: 15 g). In the case of the untreated comparison animals, massive excretion of oocysts, bloody diarrhoea and 30% mortality of the animals, which were to be attributed to the infection, took place from the seventh day after the infection.

Those doses which completely prevented, or prevented to a high degree, the excretion of oocysts and/or clinical symptoms of coccidiosis, including the mortality, were regarded as effective.

The lowest effective dosages found under the experimental conditions were lower than those of the anticoccidial medicaments which are usually employed for preventing coccidiosis in poultry. Furthermore, the compounds according to the invention—apart from having advantageous properties in respect of residues in the carcasses—are very effective against coccidiosis in mammals (Table 1).

The widespread resistance of coccidiosis towards the widely used anticoccidial agents requires more effective compounds which are derived from new classes of chemical compounds. From this point of view also, the compounds according to the invention usefully enrich the diversity of the medicaments.

TABLE 1

Comparison of the minimum effective dosages of compounds according to the present invention with those of two anticoccidial agents usually employed in practice

| Example No. | E. acervulina ppm | E. maxima ppm | E. tenella ppm | E. falciformis mg/kg |
| --- | --- | --- | --- | --- |
| 2 | 25 | 25 | 25 | 1 |
| 9 | 250 | 250 | 250 | 0.5 |
| 11 | 250 | 250 | 250 | 100 |
| 14 | 25 | 25 | 25 | 2.5 |
| 16 | 5 | 5 | 10 | 5 |
| 24 | 100 | 100 | 100 | 25 |
| 26 | 10 | 10 | 10 | 10 |
| 43 | 50 | 50 | 50 | 5 |
| 45 | 10 | 10 | 10 | 10 |
| A | 125 | 125 | 125 | 500 |
| M | 50 | 50 | 75 | 250 |

A = 1-[(4-Amino-2-propyl-5-pyrimidinyl)methyl]-2-picolinium chloride hydrochloride (known)
M = 2-(5-Ethyltetrahydro-5-(tetrahydro-3-methyl-5-(tetrahydro-6-hydroxy-6-(hydroxyethyl)-3,5-dimethylpyran-2-yl)-2-furyl)-2-furyl)-9-hydroxy-β-methoxy-α,γ,2,8-tetramethyl-1,6-dioxaspiro-(4,5)-decane-7-butyric acid (known).

PREPARATION EXAMPLE 1

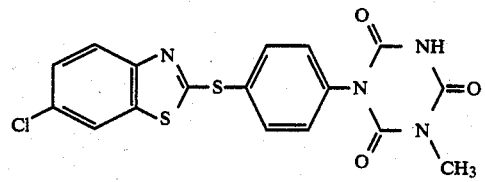

Methyl isocyanate (0.41 g) was added to a solution of 4-(6-chlorobenzothiazol-2-ylthio)-aniline (2.0 g) in pyridine (20 ml), with stirring. The mixture was stirred at room temperature for 12 hours and evaporated to dryness. The residue was dissolved in a minimal volume of boiling ethanol and the solution was cooled in a refrigerator. The resulting solid substance was collected by filtration and dried to give N-[4-(6-chlorobenzothiazol-2-ylthio)phenyl]-N'-methylurea (1.5 g), which had a melting point of 289°–291° C. This urea (1.4 g) was dissolved in 1,4-dioxane (50 ml), and chlorocarbonyl isocyanate (0.47 g) was added. The mixture was heated at the boiling point for 5 hours and evaporated to dryness. The solid residue was dissolved in a minimal volume of boiling ethanol and the solution was cooled in a refrigerator. The resulting solid substance was collected by filtration and dried to give 1.3 g of 1-[4-(6-chlorobenzothiazol-2-ylthio)phenyl]-3-methyl-1,3,5-triazine-2,4,6(1H,3H,5H)-trione of melting point 232°–233° C.

PREPARATION EXAMPLE 2

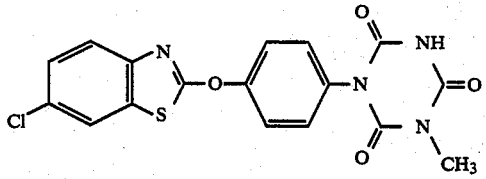

Chlorocarbonyl isocyanate (0.8 g) was added to a suspension of N-[4-(6-chlorobenzothiazol-2-yloxy)-phenyl]-N'-methylurea (2.4 g) in 1,4-dioxane (50 ml), and the mixture was heated at the boiling point for 5 hours. The mixture was evaporated under reduced pressure and the residue was dissolved in a minimal volume of boiling 1,4-dioxane. After addition of ethanol (50 ml), the clear solution was cooled in a refrigerator. The resulting solid substance was collected by filtration, washed with cold ethanol and dried to give 2.1 g of 1-[4-(6-chlorobenzothiazol-2-yloxy)phenyl]-3-methyl-1,3,5-triazine-2,4,6-(1H,3H,5H)-trione of melting point 270°-271° C. Preparation of N-[4-(6-chlorobenzothiazol-2-yloxy)phenyl]-N'-methylurea:

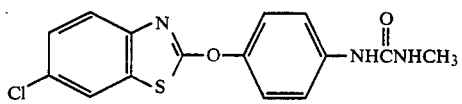

A solution of methyl isocyanate (6 g) in acetonitrile (10 ml) was added dropwise to a solution of 4-aminophenol (10.9 g) in N,N-dimethylformamide (50 ml) at 10° C. to 20° C. The mixture was stirred at 25° C. to 35° C. for 12 hours and evaporated under reduced pressure. Water (100 ml) was added to the resulting syrup and the mixture was stirred for 30 minutes. The mixture became thick in the course of stirring. The solid substance was collected by filtration, washed with cold water and recrystallized from aqueous alcohol to give 8.6 g of N-(4-hydroxyphenyl)-N'-methylurea of melting point 169°-171° C.

Anhydrous potassium carbonate (2.7 g) was added in one portion to a solution of the abovementioned urea (3.23 g) in N,N-dimethylformamide (60 ml). A solution of 2-bromo-6-chlorobenzothiazole (4.7 g) in N,N-dimethylformamide (20 ml) was added dropwise to the above suspension at 30° C. to 40° C. The mixture was stirred at 50° C. for 1 hour, at 80° C. for 1 hour and at 120° C. to 130° C. for 4 hours and then cooled. The reaction mixture was treated with water (260 ml). The solid substance formed was collected by filtration, washed with water and recrystallized from ethanol to give 4.9 g of N-[4-(6-chlorobenzothiazol-2-xyloxy)-phenyl]-N'-methylurea of melting point 225°-228° C.

The following compounds of the formula I were prepared by the same procedure as that of Preparation Example 1.

TABLE 1

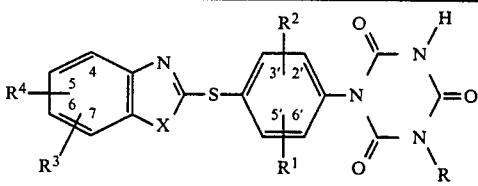

| No. | R | $R^1$ | $R^2$ | $R^3$ | $R^4$ | X | Melting point °C. |
|---|---|---|---|---|---|---|---|
| 3 | $CH_3CH_2-$ | H | H | H | H | S | 218 |
| 4 | $CH_3$ | H | H | 6-$CH_3$ | H | S | 200–202 |
| 5 | $CH_3$ | H | H | 6-$CH_3O-$ | H | S | 225–226 |
| 6 | $CH_3$ | H | H | 6-$CH_3CH_2O$ | H | S | 183–184 |
| 7 | $CH_3$ | H | H | 6-$CF_3$ | H | S | 207–215 |
| 8 | $CH_3$ | H | H | 5-Cl | H | S | 263–265 |
| 9 | $CH_3$ | H | H | 5-Cl | H | S | 205–215 |
| 10 | $CH_3CH_2$ | H | H | 5-Cl | H | S | 227–228 |
| 11 | $CH_3CH_2$ | H | H | 5-Cl | H | O | 218–221 |
| 12 | $CH_3$ | H | H | 6-F | H | O | 262–263 |
| 13 | $CH_3CH_2$ | H | H | 6-Cl | H | S | 195–205 |
| 14 | $CH_3$ | 3'-$CH_3$ | H | 6-Cl | H | S | 271–273 |
| 15 | $CH_3$ | 3'-Cl | H | 6-Cl | H | S | 271–273 |
| 16 | $CH_3$ | H | H | 6-Br | H | S | 231–232 |
| 17 | $CH_3$ | H | H | 6-I | H | S | 228–232 |

TABLE 1-continued

| No. | R | $R^1$ | $R^2$ | $R^3$ | $R^4$ | X | Melting point °C. |
|---|---|---|---|---|---|---|---|
| 18 | $CH_3$ | H | H | 5-Cl | 6-Cl | S | 215–226 |
| 19 | $CH_3$ | H | H | 4-Cl | 6-Cl | S | 218–283 |
| 20 | $CH_3$ | H | H | 4-$CH_3$ | 6-Cl | S | 300–301 |
| 28 | $CH_3$ | H | H | 6-$OCF_3$ | H | S |  |
| 29 | $CH_3$ | H | H | 6-$SCF_3$ | H | S |  |

The following compounds of the formula I were prepared by the same procedure as that of Preparation Example 2.

TABLE 2

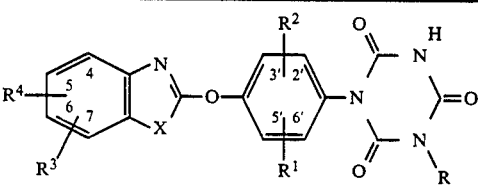

| No. | R | $R^1$ | $R^2$ | $R^3$ | $R^4$ | X | Melting point °C. |
|---|---|---|---|---|---|---|---|
| 21 | $CH_3$ | H | H | H | H | S | 256 |
| 22 | $CH_3$ | 3'-$CH_3$ | H | H | H | S | 289–296 |
| 23 | $CH_3CH_2$ | H | H | 6-Cl | H | S | 276–278 |
| 24 | $CH_3CH_2CH_2$ | H | H | 6-Cl | H | S | 227–232 |
| 25 | $CH_3$ | 3'-$CH_3$ | H | 6-Cl | H | S | 297–298 |
| 26 | $CH_3$ | 3'-Cl | 5'-Cl | 6-Cl | H | S | 280–282 |
| 27 | $CH_3$ | H | H | 6-Br | H | S | 279–281 |
| 30 | $CH_3$ | H | H | 6-$OC_2H_5$ | H | S | 227–229 |
| 31 | $CH_3$ | 3'-$CH_3$ | H | 6-$CF_3$ | H | S | 315–316 |
| 32 | $CH_3$ | 3'-Cl | 5'-Cl | 4-Cl | H | S | 228–230 |
| 33 | $CH_3$ | H | H | 5-Cl | H | S | 280–282 |
| 34 | $CH_3$ | 3'-$CH_3$ | H | 5-Cl | H | S |  |
| 35 | $CH_3$ | 3'-Cl | 4'-Cl | 5-Cl | H | S | 216–219 |
| 36 | $CH_3$ | H | H | 6-F | H | S | 276–277 |
| 37 | $C_2H_5$ | 3'-Cl | 5'-Cl | 6-Cl | H | S | 244–246 |
| 38 | $CH_3$ | H | H | 6-Cl | H | O |  |
| 39 | $CH_3$ | 3'-$CH_3$ | H | 6-Cl | H | O |  |
| 40 | $CH_3$ | 3'-Cl | 5'-Cl | 6-Cl | H | O |  |
| 41 | $CH_3$ | 3'-$CH_3$ | H | 6-Br | H | S | 299–302 |
| 42 | $CH_3$ | 3'-Cl | 5'-Cl | 6-Br | H | S | 288–293 |
| 43 | $CH_3$ | H | H | 6-J | H | S | 274–283 |
| 44 | $CH_3$ | H | H | 5-Cl | 6-Cl | S | 275–277 |
| 45 | $CH_3$ | 3'-$CH_3$ | H | 5-Cl | 6-Cl | S | 265–267 |
| 46 | $CH_3$ | 3'-$CH_3$ | 5'-$CH_3$ | 5-Cl | 6-Cl | S | 308–310 |
| 47 | $CH_3$ | H | H | 5-Cl | 6-Cl | O |  |
| 48 | $CH_3$ | 3'-$CH_3$ | H | 5-Cl | 6-Cl | O |  |
| 49 | $CH_3$ | 3'-$CH_3$ | 5'-$CH_3$ | 5-Cl | 6-Cl | O |  |
| 50 | $CH_3$ | H | H | 6-$OCF_3$ | H | S |  |
| 51 | $CH_3$ | 3'-$CH_3$ | H | 6-$OCF_3$ | H | S |  |
| 52 | $CH_3$ | 3'-Cl | 5'-Cl | 6-$OCF_3$ | H | S |  |
| 53 | $CH_3$ | H | H | 6-$SCF_3$ | H | S |  |
| 54 | $CH_3$ | 3'-$CH_3$ | H | 6-$SCF_3$ | H | S |  |
| 55 | $CH_3$ | 3'-Cl | 5'-Cl | 6-$SCF_3$ | H | S |  |
| 56 | $CH_3$ | H | H | 7-Cl | H | S | 259–261 |
| 57 | $CH_3$ | 3'-Cl | 5'-Cl | 7-Cl | H | S | 287–290 |

The following compound of the formula II were prepared by the same procedure as that given in Preparation Example 2 for the preparation of N-[4-(6-chlorobenzothiazol-2-yloxy)-phenyl]-N'-methylurea.

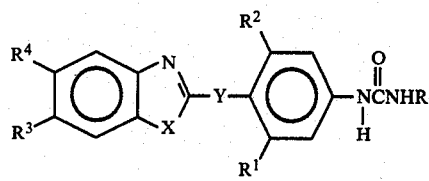

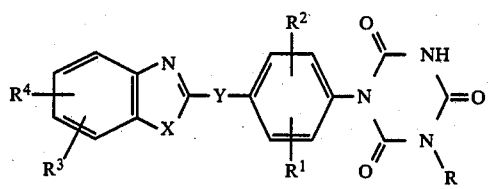

| R⁴ | R³ | X | Y | R² | R¹ | R | Melting point |
|---|---|---|---|---|---|---|---|
| H | CF₃ | S | S | H | H | CH₃ | 210–220 |
| H | CF₃ | S | S | H | H | CH₃ | 224–229 |
| Cl | Cl | S | S | H | CH₃ | CH₃ | 197–210 |
| H | Cl | O | S | H | CH₃ | CH₃ | 243–244 |
| H | Cl | S | O | H | H | CH₃ | 225–258 |
| H | Cl | S | O | H | H | C₂H₅ | 215–217 |
| H | Cl | S | O | Cl | Cl | CH₃ | 240–242 |
| H | Cl | S | O | Cl | Cl | C₂H₅ | 208–211 |
| H | Br | S | O | H | CH₃ | CH₃ | 224–228 |
| H | I | S | O | H | H | CH₃ | 246–250 |
| H | C₂H₅ | S | O | H | H | CH₃ | 217–223 |
| Cl | H | S | O | H | H | CH₃ | 199–203 |
| Cl | H | S | O | Cl | Cl | CH₃ | 253–257 |
| Cl | Cl | S | O | H | H | CH₃ | 237–239 |
| Cl | Cl | S | O | H | CH₃ | CH₃ | 238–241 |
| Cl | Cl | S | O | Cl | Cl | CH₃ | 194–195 |
| H | Cl | O | O | H | H | CH₃ | 229–234 |
| H | Cl | O | O | H | CH₃ | CH₃ | 224–225 |
| H | CF₃ | S | O | H | CH₃ | CH₃ | 215–217 |
| H | CF₃ | S | O | H | H | CH₃ | 217–218 |
| H | CF₃S | S | O | H | CH₃ | CH₃ | 209–211 |
| H | CF₃O | S | O | H | H | CH₃ | 219–221 |
| H | CF₃O | S | O | H | CH₃ | CH₃ | 192–193 |
| H | CF₃O | S | O | Cl | Cl | CH₃ | 215–220 |

It will be understood that the specification and examples are illustrative but not limitative of the present invention and that other embodiments within the spirit and scope of the invention will suggest themselves to those skilled in the art.

We claim:

1. A 1-[-(benzothia- or -oxazol-2-ylthio- or -2-yloxy)-phenyl]-1,3,5-triazine-2,4,6(1H,3H,5H)-trione of the formula in which
R is lower alkyl,
R¹ and R² each independently is hydrogen, halogen, alkyl or alkoxy,
R³ and R⁴ each independently is hydrogen, halogen, alkyl, alkoxy, alkylthio, fluoroalkyl, fluoroalkoxy or fluoroalkylthio, and
X and Y each independently is sulphur or oxygen, or a salt thereof.

2. A compound or salt according to claim 1, in which
R is $C_{1-4}$-alkyl,
R¹ and R² each independently is hydrogen, chlorine or $C_{1-4}$-alkyl,
R³ is halogen, $C_{1-4}$-alkyl, $C_{1-4}$-alkoxy, $C_{1-4}$-halogenoalkoxy, $C_{1-4}$-halogenoalkyl, $C_{1-4}$-alkylthio or $C_{1-4}$-halogenoalkylthio, and
R⁴ is hydrogen or halogen.

3. A compound or salt according to claim 1, in which
R is methyl, ethyl or propyl,
R¹ and R² each independently is hydrogen, chlorine or methyl, in the 3'- or 5'-position,
R³ is fluorine, chlorine, bromine, iodine, methyl, ethyl, methoxy, ethoxy, methylthio, trifluoromethyl, trifluoromethoxy or trifluoromethylmercapto, and
R⁴ is hydrogen or chlorine.

4. An anticoccidial composition comprising an anticoccidially effective amount of a compound or salt according to claim 1 in admixture with a pharmaceutically acceptable diluent.

5. A method of combating coccidiosis in mammals and poultry which comprises administering thereto an anticoccidially effective amount of a compound or salt according to claim 1.

6. An animal feed composition comprising an edible base and from about 5 ppm up to 20% by weight of a compound or salt according to claim 1.

* * * * *